US008818561B2

(12) United States Patent
Koehler et al.

(10) Patent No.: US 8,818,561 B2
(45) Date of Patent: Aug. 26, 2014

(54) SLUMP FLOW MONITORING (75) Inventors: Eric Koehler, Cincinnati, OH (US);
Steve Verdino, Hamilton, OH (US);
James Klauke, Miamisburg, OH (US);
Robert Culley, West Chester, OH (US);
Joseph Sostaric, Danville, CA (US)

(73) Assignee: Verifi LLC, West Chester, OH (US)

( * ) Notice: Subject to any disclaimer, the term of this patent is extended or adjusted under 35 U.S.C. 154(b) by 335 days.

(21) Appl. No.: 13/258,104

(22) PCT Filed: Aug. 7, 2009

(86) PCT No.: PCT/US2009/053082
§ 371 (c)(1),
(2), (4) Date: Sep. 21, 2011

(87) PCT Pub. No.: WO2010/110814
PCT Pub. Date: Sep. 30, 2010

(65) Prior Publication Data
US 2012/0016523 A1 Jan. 19, 2012

Related U.S. Application Data (60) Provisional application No. 61/164,196, filed on Mar. 27, 2009.

(51) Int. Cl.
*G05B 21/00* (2006.01)
*G01N 33/38* (2006.01)
*G01N 11/00* (2006.01)

(52) U.S. Cl.
CPC ........ *G01N 11/00* (2013.01); *G01N 2011/0046* (2013.01); *G01N 33/383* (2013.01)

USPC ........................................................ 700/265

(58) Field of Classification Search
USPC ........................................................ 700/265
See application file for complete search history.

(56) References Cited

U.S. PATENT DOCUMENTS

| 4,008,093 | A | 2/1977 | Kitsuda et al. |
| 4,900,154 | A | 2/1990 | Waitzinger et al. |
| 5,713,663 | A | 2/1998 | Zandberg et al. |
| 6,227,039 | B1 | 5/2001 | Te'eni |
| 6,484,079 | B2 | 11/2002 | Buckelew et al. |
| 6,611,755 | B1 | 8/2003 | Coffee et al. |
| 7,510,319 | B2 * | 3/2009 | Hood .............................. 366/59 |

(Continued)

OTHER PUBLICATIONS

International Preliminary Report on Patentability/Written Opinion mailed Oct. 6, 2011 in corresponding PCT application No. PCT/US2009/053082, 9 pages.

(Continued)

*Primary Examiner* — Mohammad Ali
*Assistant Examiner* — Ziaul Karim
(74) *Attorney, Agent, or Firm* — Craig K. Leon (57) ABSTRACT Method and system for monitoring slump flow of hydratable cementitious material such as wet concrete in a rotating mixing drum. Whereas prior art methods use a single value of the hydraulic pressure for turning the drum (such as the average value) and correlating with slump values using the vertical drop measurements of the standard slump test (e.g. ASTM C 143-05), the present invention involves analysis of values corresponding to slump flow of concrete samples, preferably having slump flow values of 16-36 inches when measured using standard slump flow tests (e.g., ASTM C1611-05).

12 Claims, 4 Drawing Sheets

(56) References Cited

U.S. PATENT DOCUMENTS

| | | |
|---|---|---|
| 2002/0015354 A1 | 2/2002 | Buckelew |
| 2002/0154029 A1* | 10/2002 | Watters et al. ........... 340/870.07 |
| 2005/0141338 A1 | 6/2005 | Jarvinen et al. |
| 2007/0185636 A1 | 8/2007 | Cooley et al. |
| 2008/0316856 A1 | 12/2008 | Cooley et al. |
| 2009/0037026 A1 | 2/2009 | Sostaric et al. |
| 2012/0180872 A1* | 7/2012 | Hilton et al. ...................... 137/1 |

OTHER PUBLICATIONS

International Search Report dated Sep. 21, 2009 in corresponding PCT application No. PCT/US2009/053082, 1 page.

ASTM International, Designation: C 1611/C 1611M-05, "Standard Test Method for Slump Flow of Self-Consolidating Concrete", 6 pages, Sep. 2005.

ASTM International, Designation: C 143/C 143M-05, "Standard Test Method for Slump of Hydraulic-Cement Concrete", 4 pages, May, 2005.

* cited by examiner

SLUMP FLOW MONITORING

This application claims priority of U.S. Provisional Ser. No. 61/164,196 filed Mar. 27, 2009, the disclosure of which is incorporated herein by reference.

FIELD OF THE INVENTION

The present invention relates to manufacturing of concrete, and more particularly to a method for monitoring and controlling the slump flow of hydratable cementitious material such as wet concrete in a mixing drum.

BACKGROUND OF THE INVENTION

It is known to monitor and control the "slump," or fluidity property, of concrete in ready-mix delivery trucks by using sensors to monitor the energy required for rotating the mixing drum (e.g., U.S. Pat. No. 4,008,093) and/or the torque applied to the drum by hydraulic pressure (e.g., U.S. Pat. No. 5,713,633). The higher the amperage or hydraulic pressure needed to turn the drum at a given speed, the stiffer or less flow-able (lower slump) the concrete mixture.

Automated control systems enable transportation of concrete in mixer trucks over longer distances by allowing for adjustment of slump in transit through the addition of water or other liquids. A hydraulic sensor coupled to the hydraulic drive and/or a rotational speed sensor connected to the drum may be used for monitoring purposes. Such sensors can be wirelessly connected to a computer processing unit and a wireless communication system to permit modifications to be made during operation. See e.g., U.S. Ser. No. 10/599,130 (Publication No. 2007/01856A1).

The monitoring of concrete slump involves calibrating the outputs or values obtained from the hydraulic sensor and/or electrical sensor on a mixing truck, and correlating these with slump values obtained using a standard slump cone test. In the standard slump cone test, a 12-inch truncated cone containing fresh concrete is removed to permit the concrete to drop, and the vertical height drop of the concrete is measured (e.g. ASTM C143-05). Concrete having this known slump property is added into a rotatable drum mixer so that a hydraulic or electrical value, obtained as an output from the sensor, can be stored into a memory location and subsequently correlated by a computer processing unit. During the delivery of the concrete to a customer, the concrete stiffens with time as a result of hydration, evaporation, and other factors, and the sensors detect this as increased hydraulic or electrical energy required for turning the mixing drum. The on-board computer processing unit compares the detected energy value obtained from the sensor or sensors and compares this to a value or value range stored in computer-accessible memory. If the sensors and computer processing unit (CPU) detect that the concrete is beginning to stiffen, the CPU can then be triggered to activate metering or pumping devices to inject water or other liquid (e.g., chemical dispersant) into the concrete to restore the slump to the desired value.

Other methods are available for manually measuring workability (which is defined by the American Concrete Institute as the ease and homogeneity with which the concrete can be mixed, placed, consolidated, and finished), but these have not been disclosed or suggested for use in automated monitoring systems.

As an example, for highly flowable concrete mixtures such as self-consolidating concrete, the "slump flow" test is used (e.g. ASTM C 1611-05). In this test, concrete is placed in a standard slump cone, the cone is removed, and the horizontal spread—rather than the vertical drop—is measured. For highly flowable mixtures, measurements of the slump (vertical drop) cannot be used because such measurements would not give meaningful information about the workability of the concrete.

The present inventors believe that a major problem of current slump monitoring information obtained by using automated systems is that such equipment provides only information about slump. An objective of the present invention, therefore, is to include "slump flow" test data in automated control systems and methods, so as to provide enhanced capabilities in monitoring and controlling cementitious materials during mixing and/or delivery operations.

Concrete batches are loaded into a concrete mixer on the basis of a mixture design, mixture proportion, or mixture recipe. These three terms are used interchangeably herein. The mixture design stipulates the amounts of all materials to be used in the concrete batch. Concrete batched according to a certain design is expected to achieve certain workability—such as slump or slump flow—and certain hardened properties—such as strength and durability.

Therefore, when batching a load of concrete in a mixer, it is important to batch the correct amounts of all materials. Frequently, however, variations occur in the quantity of materials batched, especially in the water content. Having the correct design water is critical to ensuring that design workability and hardened properties are achieved consistently. Even a small change in water can significantly affect the workability and hardened properties. If too much water is added to a batch of concrete, the concrete will segregate and the strength and durability of the hardened concrete will be reduced. If too little water is added, the concrete will lack adequate workability for successful placement and may be described as "sticky" or "viscous."

Water is added to a batch of concrete in multiple ways: metered batch water, aggregate free water, post-batch truck added water, residual drum water, and unintentionally added water. The aggregate free water is difficult to measure and may be highly variable during a production. Even moisture probes placed in an aggregate bin before the aggregate is loaded into the mixer are of limited accuracy. Truck operators can be instructed to empty the drum of all residual water and to avoid any unintentionally added water; however, this is not always done completely, if at all. The metered batch water is typically the most accurate measurement. Consequently, significant variation may occur in the total water content of a concrete batch. The variations in total water content of the concrete mixture cause variations in the workability and hardened properties. In contrast, the addition of additional cement dispersant (chemical admixture) has a relatively small affect on hardened properties in comparison to water. Therefore, a mixture with excess cement dispersant may be too fluid but have adequate strength, whereas a mixture with excess water content may be too fluid and have inadequate (low) strength.

In current slump monitoring equipment, it is known to add water, chemical admixtures, or both to adjust the slump or hydraulic pressure to a pre-determined target. Both water and certain chemical admixtures—such as cement dispersants—are known to increase slump and reduce the hydraulic pressure to rotate a mixing drum. However, if the slump or hydraulic pressure is above or below the pre-determined target, it is not apparent whether this discrepancy is due to incorrect water or chemical admixture content.

The present inventors believe that a major problem of current slump monitoring equipment is the lack of a method for determining whether to add water, chemical admixtures, or both and in what quantities to add such materials so that the correct workability and hardened properties are achieved consistently for a given mixture design. An objective of the present invention, therefore, is to provide such a method.

Additionally, the present inventors believe that the present invention provides a method for determining whether to add water, chemical admixtures, or both to achieve the correct workability and hardened properties of concrete manufactured in a stationary central mixing device as typically used in concrete mixing plants Hence, a novel method and system for monitoring and adjusting concrete rheological properties in mixing drums and other mixing devices are needed.

SUMMARY OF THE INVENTION

The present invention provides a method and system for monitoring rheology of a cementitious material, such as concrete, being mixed in a rotatable mixing drum, through the use of slump flow test data.

Thus, an exemplary method of the present invention for mixing a cementitious material, comprises:
(A) rotating a mixing drum containing a hydratable cementitious material therein;
(B) providing a sequence of values corresponding to hydraulic pressure required to rotate said mixing drum at a particular speed $V^1$ and calculating an average value based on said sequence of values;
(C) comparing said calculated average value to a set of average values at speed $V^1$ previously stored in computer memory storage location, said previously stored set containing values obtained from hydratable cementitious materials having predetermined slump flows at various slump flows within the range of 16 inches to 36 inches determined by horizontal spread of cementitious materials released from a slump cone (e.g., in accordance with a standard cone test such as ASTM C1611-05); and
(D) providing an indication of slump flow corresponding to said calculated average value provided in (B); adjusting the slump flow of said hydratable cementitious material in said mixing drum based on comparing said calculated average value to a set of average values previously stored in computer memory storage location; or performing a combination thereof.

The indication of slump flow value can be provided such as by computer monitor display or printed on paper or otherwise entered as data into a computer memory storage location.

The slump flow of the hydratable cementitious material can be adjusted by addition of a liquid (e.g., water, chemical admixture(s), or combination thereof) into the hydratable cementitious material, based on the comparison of obtained value with pre-stored slump flow values.

The tilt or inclination of the mixing drum, concrete load size, temperature of the concrete, or some combination thereof may also be taken into account when providing the slump flow of the cementitious material and its adjustment using water and/or chemical admixture.

An exemplary system of the invention for monitoring slump flow, comprises: a rotatable mixing drum for mixing a hydratable cementitious material, a sensor for measuring hydraulic pressure required for rotating said mixing drum, a sensor for measuring rotational speed of said mixing drum, a computer processing unit for receiving values from said sensor for measuring hydraulic pressure required for rotating said mixing drum and for receiving values from said sensor for measuring rotational speed of said mixing drum, and computer memory storage location having stored therein a set of values obtained from hydratable cementitious materials having predetermined slump flows at various slump flows within the range of 16 inches to 36 inches determined by employing manual measurement of horizontal spread of cementitious materials released from an inverted and removed slump cone (e.g., in accordance with a standard cone test, such as ASTM C1611-05).

Further advantages and features of the invention may be described hereinafter.

BRIEF DESCRIPTION OF THE DRAWINGS

Further advantages and features of the present invention may be more readily comprehended when the following detailed description of preferred embodiments is taken in conjunction with the appended drawings wherein.

DETAILED DESCRIPTION OF EXEMPLARY EMBODIMENTS

The term "cementitious" as used herein refers to a material that comprises portland cement or portland cement substitutes which otherwise function as a binder to hold together fine aggregates (e.g., sand), coarse aggregates (e.g., crushed stone or gravel), or mixtures thereof.

Such cementitious materials may further include fly ash, granulated blast furnace slag, lime stone, or natural pozzolans, which may be combined with Portland cement or be used to replace or substitute for a portion of the portland cement without serious diminishment of hydratable properties. Incidentally, a "mortar" refers to cement or cementitious mixture having a fine aggregate such as sand; while "concrete" refers more accurately to a mortar that also contains a coarse aggregate such as crushed stone or gravel. The use of the term "cementitious material" may be used interchangeably with the term "concrete," as concrete is most commonly provided by ready-mix trucks which have rotatable mixing drums, but the term "concrete" as used herein does not necessarily exclude the fact that the present invention can be used for delivering materials that contain only cement or cement substitutes (e.g., pozzolans) or mortars.

Cementitious materials deemed to be "hydratable" are those which harden by chemical interaction with water.

Cementitious materials may further contain chemical admixtures, such as water-reducing agents or high range water-reducing agents, viscosity modifying agents, corrosion-inhibitors, shrinkage reducing admixtures, set accelerators, set retarders, air entrainers, air detrainers, pigments, colorants, fibers for plastic shrinkage control or structural reinforcement, and the like.

Concrete delivery mixing trucks having slump control monitoring and control equipment, such as hydraulic and/or electric sensors for measuring the energy for turning the mixing drum, speed sensors for measuring the speed of rotation, temperature sensors for monitoring the atmospheric temperature as well as the mix temperature, and dispensing equipment, as well as the computer processing units for monitoring signals from the sensors and actuating the dispensing equipment are by now relatively well known in the industry. For example, such slump control systems, which can be used in association with wireless communication systems, are disclosed in U.S. Pat. No. 5,713,663; U.S. Pat. No. 6,484,079; U.S. Ser. No. 09/845,660 (Publication no. 2002/0015354A1); U.S. Ser. No. 10/599,130 (Publication no. 2007/01856A1); Ser. No. 11/764,832 (Publication no. 2008/0316856); and Ser. No. 11/834,002 (Publication no. 2009/0037026). A further exemplary system for monitoring and control using wireless communications in combination with sensors for monitoring various physical properties of the concrete mix is taught in U.S. Pat. No. 6,611,755 of Coffee. These teachings are incorporated herein by reference.

Exemplary mixing drums contemplated for use in the present invention are rotatably mounted on delivery trucks, and these mixing drums have an inner surface upon which the at least one mixing blade is attached to the inner surface such that said at least one mixing blade rotates with the mixing drum.

In view of the foregoing teachings, the present inventors believe that a number of exemplary embodiments of the invention may be practiced using conventional automated concrete mix monitoring equipment with slight modifications as would be apparent in view of the invention disclosed herein. Such mix monitoring equipment is available under the VERIFI® name from Grace Construction Products, Cambridge, Mass., and RS Solutions LLC, West Chester, Ohio.

Exemplary methods of the invention for monitoring a cementitious material, and specifically to correlate hydraulic pressure readings with slump flow of the cementitious material, comprise: rotating a mixing drum containing a hydratable cementitious material therein; providing a sequence of values corresponding to hydraulic pressure required to rotate said mixing drum at a particular speed $V^1$ and calculating an average value based on said sequence of values; comparing said calculated average value to a set of average values at speed $V^1$ previously stored in computer memory storage location, said previously stored set containing values obtained from hydratable cementitious materials having predetermined slump flows at various slump flows within the range of 16 inches to 36 inches determined by employing manual measurement of horizontal spread of cementitious materials released from an inverted and removed slump cone (e.g., in accordance with a standard cone test such as ASTM C1611-05); and providing an indication of slump flow corresponding to said calculated average value, adjusting the slump flow of said hydratable cementitious material in said mixing drum based on comparing said calculated average value to a set of average values previously stored in computer memory storage location, or performing a combination thereof. The indication of the slump flow value can be provided by computer monitor display or printed paper output. This value of slump flow can of course be entered as data into computer memory storage location.

All references to procedures of the ASTM procedures shall be taken to refer to the latest publication before the priority filing date of this application, unless otherwise indicated.

In preferred methods and systems of the invention, both slump and slump flow values for hydratable cementitious materials may be stored in computer memory storage location, using conventional automated concrete mix monitoring equipment.

For example, the slump (vertical drop) is appropriate for relatively stiff mixtures and the slump flow (horizontal spread) is appropriate for relatively fluid mixtures. The slump cone is 12 inches in height; therefore, the maximum vertical drop that can be measured is approximately 11 inches— depending on the size of the crushed stone or gravel in the concrete mixture. A typical maximum aggregate size for concrete is one inch, which would correspond to a maximum slump measurement of 11 inches. For mixtures exhibiting a slump of 0 to 11 inches, differences in slump are indicative of differences in workability. When the slump is approximately equal to or greater than 11 inches, further increases in workability are not detectable with the slump test. Instead, slump flow can be measured. Changes in slump flows within the range of 16 to 36 inches are typically indicative of differences in workability of highly flowable concrete mixtures.

Figure 1:
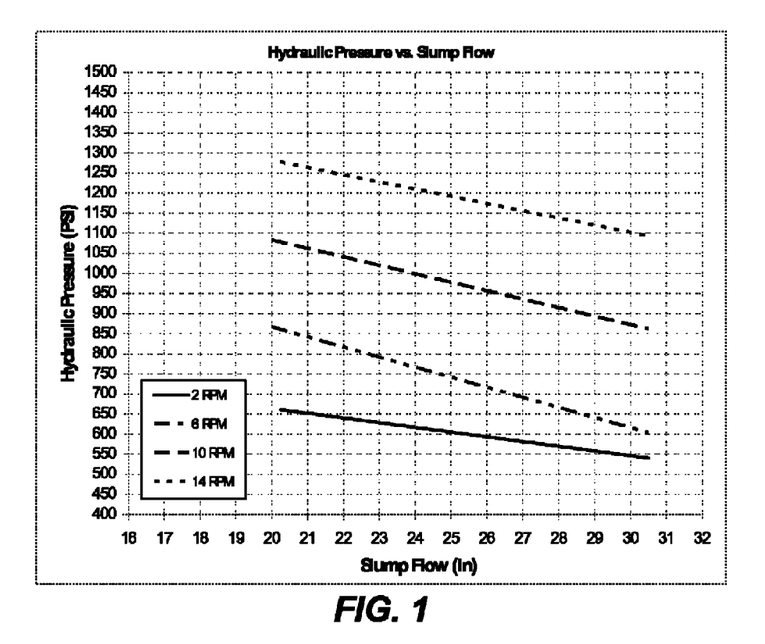
FIG. 1 is a graphic illustration of the correlation between slump flow and the hydraulic pressure required to rotate a loaded mixing drum at various speeds.

FIG. 1 shows the relationship between slump flow and the hydraulic pressure required to rotate the mixing drum at various speeds. The data upon which this graphic illustration was based was generated as part of the calibration for the mixer and is maintained in computer memory storage location for calculation of slump flow from hydraulic pressure and drum speed measurements. Slump flow was measured manually in accordance with ASTM C 1611. Using FIG. 1 as an example, if the drum speed is measured as 3.4 rpm and the hydraulic pressure is measured as 717 psi, the slump flow would be calculated as 21.5 inches.

Figure 2:
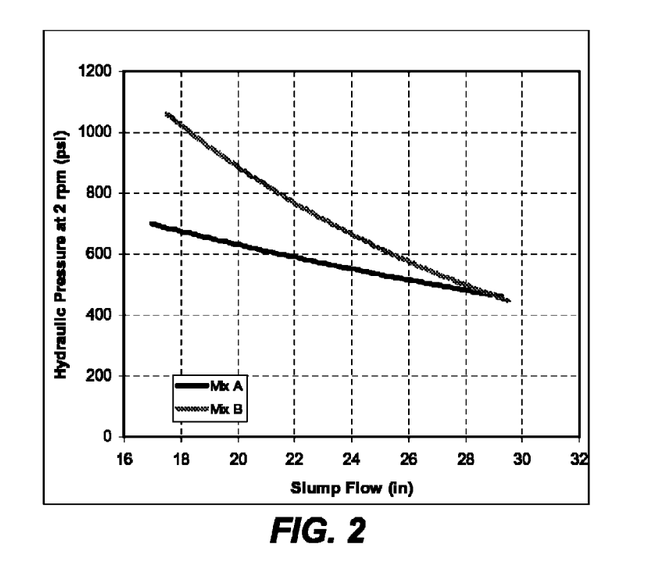
FIG. 2 is a graphic illustration of the correlation between slump flow and the hydraulic pressure required to rotate the loaded mixing drum at 2 rpm for two different mixture designs.

The calculation of slump flow from measured truck data can be further enhanced by using different curves of slump flow versus hydraulic pressure and drum rotation speed for different mixture designs. FIG. 2 shows that the slump flow versus hydraulic pressure relationship can vary for different mixture designs. The two different mixture designs shown in the figure were made with different materials and proportions of materials, but were mixed and measured in the same mixing drum. To implement the use of different curves, the provided average hydraulic pressure at a given speed is compared to the slump flow versus hydraulic pressure data stored in computer memory location for the given mixture design in the mixing drum. The data memory location may store data for multiple mixture designs for the given mixing drum. This process would require determining the mix design ID corresponding to the batch of concrete in the drum in order to choose the correct calibration curve. In many cases, similar mixture designs may be able to use the same calibration curve stored in computer memory, despite varying in materials or relative proportions of materials. In fact, it is possible in some cases to use one curve for all mixtures commonly produced in a single concrete mixer.

Similarly for slump, different hydraulic pressure vs. slump curves can be used for different mixture designs. Indeed, FIG. 3 shows how curves generated for two different mixture designs can vary.

Figure 3:
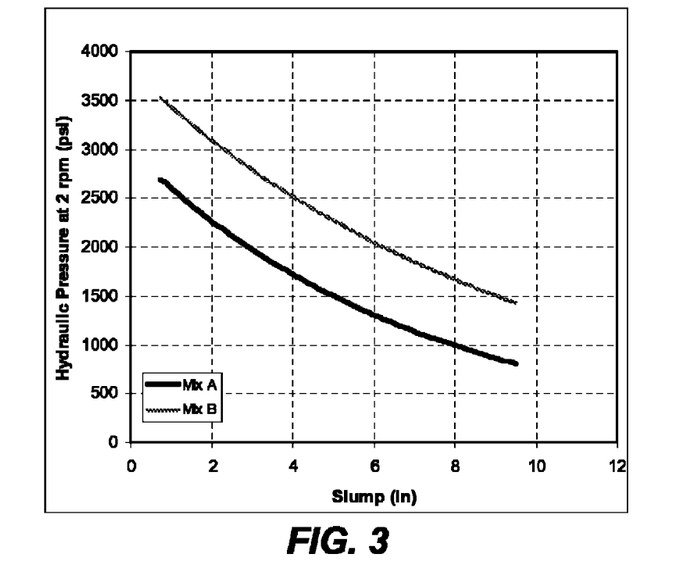
FIG. 3 is a graphic illustration of the correlation between slump and the hydraulic pressure required to rotate the loaded mixing drum at 2 rpm for two different mixture designs.

Other factors not represented in FIGS. 1 to 3 may affect the hydraulic pressure measured at a given speed for a given slump flow in a given drum. These factors include drum tilt, load size, load weight, build-up of hardened concrete within the drum, truck hydraulic equipment, truck acceleration or deceleration, and vibration from vehicle travel (e.g. bumps in road). The calculated slump flow can be adjusted based on these factors, or not reported in such cases as when severe road vibration distorts readings.

Figure 4:
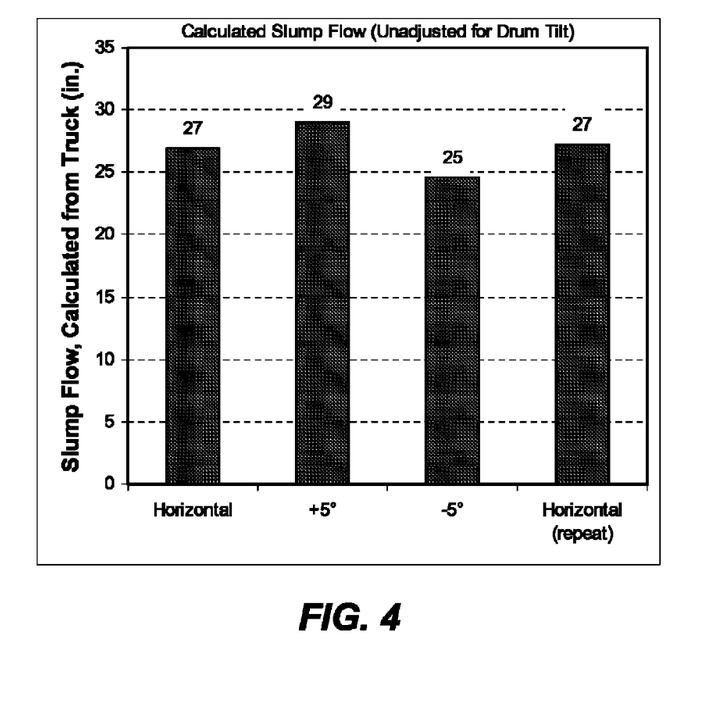
FIG. 4 is a graphic illustration showing the effect of drum tilt on slump flow calculated from truck hydraulic pressure and drum rotation speed measurements.

FIG. 4 shows the effect of drum tilt on the slump flow calculated from truck measurements. As the angle of the truck is changed from horizontal to 5 degrees from horizontal, the slump flow calculated from truck measurements varies by +/−2 inches. Therefore, it is necessary to adjust the slump flow calculation based on the tilt of the drum. Note that the angles are shown in reference to the truck—the drum is mounted at an angle to the horizontal truck frame.

The truck hydraulic system can also introduce variations in slump and slump flow calculations. These variations can be reduced by evaluating both the "charge" and "discharge" hydraulic pressure ports on the hydraulic system. The hydraulic drive system for concrete mixers consists of a pump-motor combination to turn the drum. The pump is driven by a power take-off (PTO) drive shaft from the truck engine, the output of which varies based on the engine speed. The hydraulic motor is a fixed displacement type and contains the test ports for the pressure sensors used to calculate slump or slump flow as described herein. To overcome the effect of varying engine speeds and provide adjustable drum speeds, the pump is a variable displacement type and is used along with a manual or electronic displacement control. However, these systems do not provide any feedback in the form of pressure and only some provide drum speed feedback. Therefore, variations in engine speed and pump output will cause pressure fluctuations in the resulting pressure measured from the hydraulic ports on the hydraulic motor and used to represent the concrete properties. Furthermore, the hydraulic system has internal valves and a charge pump to control and divert the flow required to prime, lubricate and cool the system. The valves are pressure relief type and will open and close based on their breaking pressures versus the system pressure at any given time. This introduces another layer of fluctuations in hydraulic pressures that are not related to the properties of the concrete in the drum.

The hydraulic motor contains at least two ports, indicated herein as "charge" and "discharge" ports. Generally, as the energy to rotate the mixing drum in charge direction increases, the hydraulic pressure on the charge port increases more significantly than the hydraulic pressure on the discharge port. Conversely, as the energy to rotate the mixing drum in the discharge direction increases, the hydraulic pressure on the discharge port increases more significantly than the hydraulic pressure on the charge port.

Figure 5:
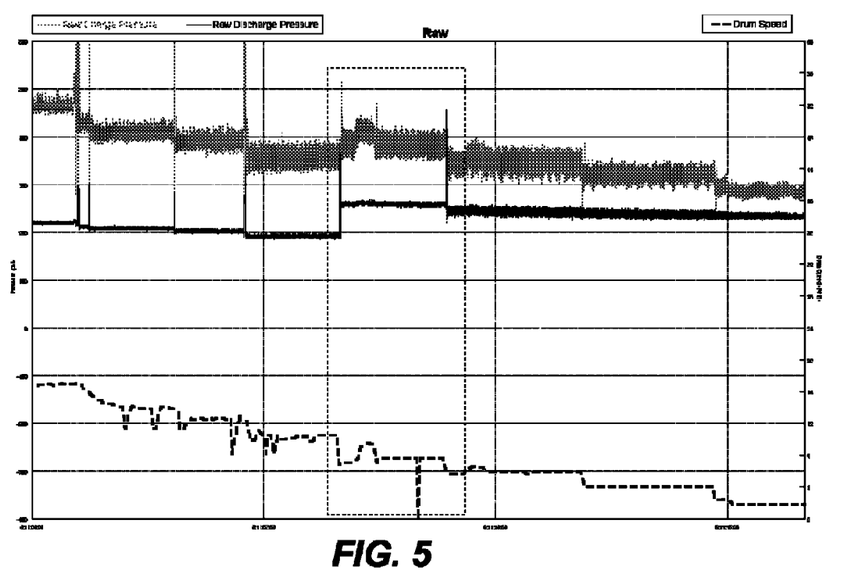
FIG. 5 is a graphic illustration showing drum speed and hydraulic pressure from the charge port of the hydraulic pressure system of a concrete mixing drum.

By observing the pressures on both the charge and discharge ports, one can determine what noise is caused by the hydraulic system and engine and differentiate those signals from the pressure signal coming from mixing and/or agitating the material in the drum. FIG. 5 shows the hydraulic pressure measured on the charge port. As the drum speed decreases, so should the hydraulic pressure required to mix or agitate the material. The boxed area in FIG. 5 shows a rise in pressure for a decrease in drum speed caused by the hydraulic system operation and not related to the properties of the concrete in the mixer. Also it shows the subsequent steps to the right of the boxed section are artificially elevated, even though they are measured with decreasing drum speed. This causes false readings and subsequent inaccuracies in the measurements related to the concrete mix in the drum.

Figure 6:
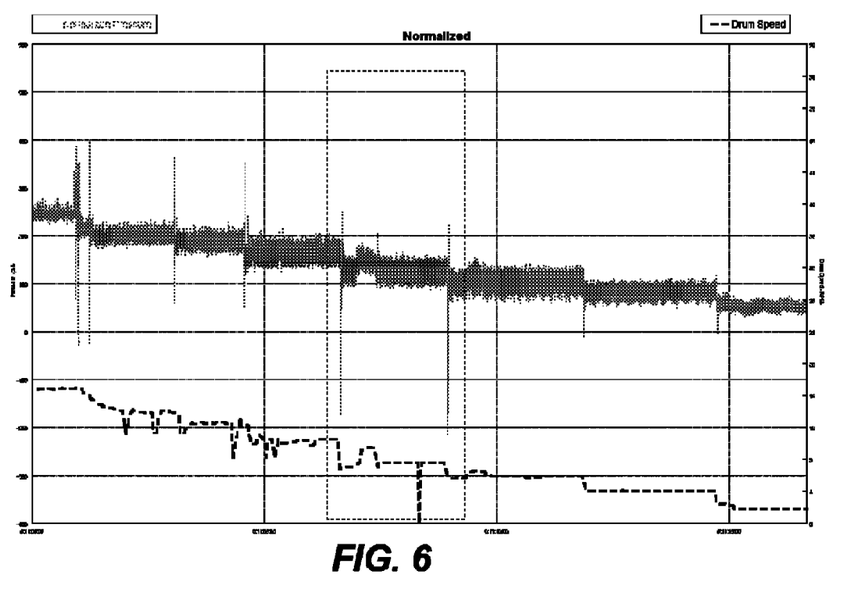
FIG. 6 is a graphic illustration showing drum speed and the normalized hydraulic pressure, calculated as a function of the pressure from both the charge and discharge ports of the hydraulic pressure system of a concrete mixing drum.

To compensate for these system fluctuations the discharge pressure is used to normalize the pressure by an algorithm including charge pressure, discharge pressure, and drum speed to calculate the actual pressure required to mix and/or agitate the concrete mix. FIG. 6 shows the result of this compensation. The boxed area shows that the corrected, normalized hydraulic pressure measurement decreases with drum speed. The resulting pressure curve now follows the drum speed. In FIG. 6, the normalized hydraulic pressure was calculated as the difference between the charge and discharge pressure.

Figure 7:
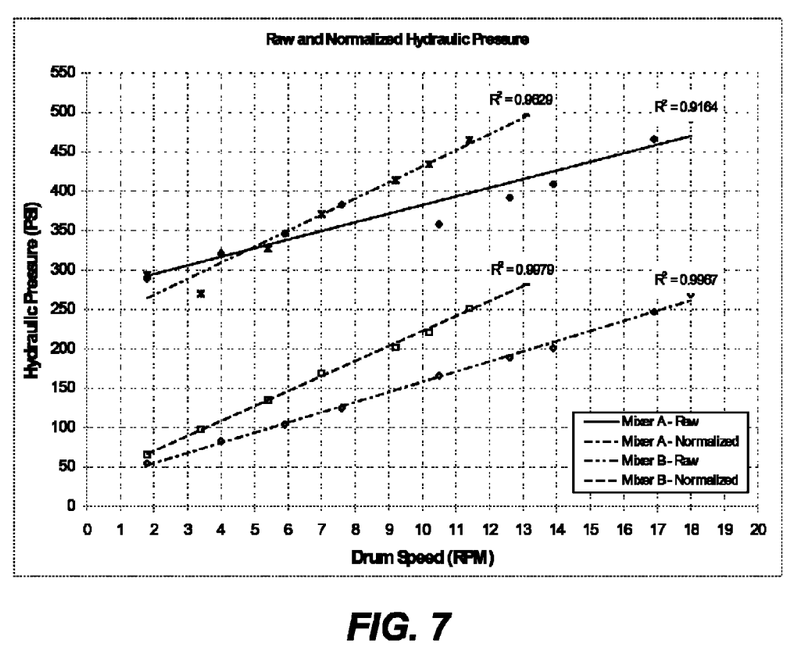
FIG. 7 is a graphic illustration showing the correlation between drum speed and hydraulic pressure where hydraulic pressure is determined as raw hydraulic pressure (pressure measured from charge port) and normalized hydraulic pressure (a function of pressures measured from both charge and discharge ports)

FIG. 7 demonstrates how normalizing the hydraulic pressure data provides an increase in the linearity between hydraulic pressure and drum speed for a empty drum, as indicated by the coefficient of determination, $R^2$.

When the slump flow of a concrete mixture is too low, the slump flow can be adjusted by adding water or chemical admixture. When adjusting a concrete mixture to a certain pre-determined target slump flow, it is important to determine whether to add water, admixture, or a combination of water and admixture. Adding water and certain chemical admixtures (e.g. a cement dispersant such as a water reducer, including high range water reducers known as superplasticizers) will both increase slump flow. If too much water is added, the concrete mixture will exhibit segregation and the strength of the concrete will be reduced, even if the concrete mixture exhibits the correct slump flow. In this case, the correct slump flow could be achieved, despite excessive water content, by reducing the chemical admixture dose. If too little water is added, the concrete mixture may be highly viscous and difficult to pump and place, even if the concrete mixture exhibits the correct slump flow. In this case, the correct slump flow could be achieved despite the deficient water content by increasing the chemical admixture dose. Therefore, simply achieving the correct slump flow for a given mixture design is inadequate for assuring that the correct workability and hardened properties are achieved.

The determination of the correct amounts of water and chemical admixture can be accomplished by measuring both slump and slump flow, but at different times for a given batch, and comparing these to target slump and slump flow values for the given mixture design. For instance, the concrete mixture can be batched by withholding a certain pre-determined portion of the chemical admixture needed to achieve the high level of flowability associated with a particular concrete mixture design (i.e. the target slump flow). After the concrete is initially mixed, the slump is measured with automated slump-monitoring equipment. If this slump is less than a certain pre-determined target slump (which is measured before the remainder of the withheld chemical admixture is added into the concrete mixture), sufficient water is added to the concrete mixture to achieve the pre-determined target slump. The necessary quantity of chemical admixture is also added to change the concrete flowability from the pre-determined target slump to the pre-determined target slump flow. The amount of chemical admixture may be further adjusted due to variations in factors—such as concrete temperature, transit time, and materials—in order to ensure that the concrete is at the correct slump flow at the time of discharge from the mixer and that the design water content is not exceeded. Furthermore, the initial pre-determined target slump may be adjusted based on concrete temperature to ensure more accurate water content. For instance, increased concrete temperature typically results in lower slump at constant water content, thus requiring the predetermined target slump to be decreased to maintain constant water content.

In an exemplary method of the invention, wherein slump flow of a hydratable cementitious material in a rotating mixing drum is monitored, the water content of said hydratable cementitious material is adjusted to achieve a predetermined target slump within the range of 0 to 10 inches, and subsequently chemical cement dispersant is introduced to adjust the slump flow of said hydratable cementitious material to a pre-determined target slump flow within the range of 16 to 36 inches. The slump flow is then likely to decrease with time due to hydration and loss of cement dispersant effectiveness. As a result, additional cement dispersant is added to maintain the slump flow with time. Preferably, the water adjustments are made as quickly as possible.

Alternatively, in another exemplary method of the invention, wherein slump flow of a hydratable cementitious material in a rotating mixing drum is monitored, water is introduced to adjust the slump flow of said hydratable cementitious material to a pre-determined target slump flow within the range of 16-36 inches and subsequent maintenance of the slump flow with time is achieved by adjusting cement dispersant quantity. In this case, a certain amount of cement dispersant is added prior to water adjustment. A portion of the water is added during the initial batching and only the final adjustment of the water content is made in the truck based on slump flow measurements. The amount of cement dispersant may be adjusted based on factors such as temperature to increase the accuracy of the water content adjustment. Preferably, the water adjustments are made as quickly as possibly.

In further exemplary methods and systems of the invention, various data sets may be stored in computer memory storage location which contain values corresponding to slump flow as well as slump (e.g., for all slump values between 0 and 12 inches and all slump flow values between 8 and 36 inches and more preferably at least between 16 and 36 inches) and the torque readings (i.e., values corresponding to the hydraulic energy required to rotate the mixing drum at these various slump flow and slumps), using both water and chemical cement dispersant. Thus, for example, if the truck delivery operator wants to use water for adjusting the slump of the concrete between 0-12 inches, and then to use a chemical cement dispersant to adjust slump flow of the concrete in the much higher slump flow range of 18-32 inches, for example, the operator will be able to calibrate the system to compare obtained torque readings using the proper control calibration, and the system will then be able to introduce the appropriate liquid (water and/or chemical cement dispersant) at the appropriate time in order to adjust the slump or slump flow of the cementitious material in the mixing drum at the appropriate time and in the appropriate amount, so as to meet a pre-determined or pre-selected slump or slump flow characteristic desired. Conversely, the truck delivery operator may want to use only chemical cement dispersants at slump of 1-12 inches, but water at slump flows of 18-32, and will be able to calibrate the system to compare obtained torque readings using the proper control calibration, and the system will then be able to introduce the appropriate liquid (water and/or chemical cement dispersant) at the appropriate time in order to adjust the slump or slump flow of the cementitious material in the mixing drum at the appropriate time and in the appropriate amount, so as to meet a pre-determined or pre-selected slump or slump flow characteristic desired.

In other words, if the system is instructed to maintain the cementitious mix in the rotating mixing drum at a particular slump or slump flow level, and it is desired to add a liquid (water and/or chemical cement dispersant) into the concrete mix, then the torque reading obtained from real-time monitoring of the hydraulic pressure required to rotate the drum should be compared to the appropriate control data stored in computer memory. Thus, if water is the liquid to be introduced into the concrete mix, the torque readings obtained should be compared to pre-stored data obtained using water. Alternatively, if chemical cement dispersant is desired to be introduced into the concrete mix, the torque readings obtained should be compared to pre-stored data obtained using the particular chemical cement dispersant. Thus, where the torque readings are increasing beyond a desired range, indicating the slump or slump flow of the concrete mix is stiffening beyond the target range, then the appropriate amount of liquid (whether it be water, chemical cement dispersant, or combination of both) can be accurately dosed into the concrete mix because the appropriate control data will have been used as control.

It is also possible to use the present invention to ensure the correct admixture and water content in mixtures where the final workability is less flowable and more appropriately characterized by slump, not slump flow. In such cases, the pre-determined target slump flow would be replaced by a second pre-determined target slump, where this second pre-determined target slump is greater than the first pre-determined target slump.

Figure 8:
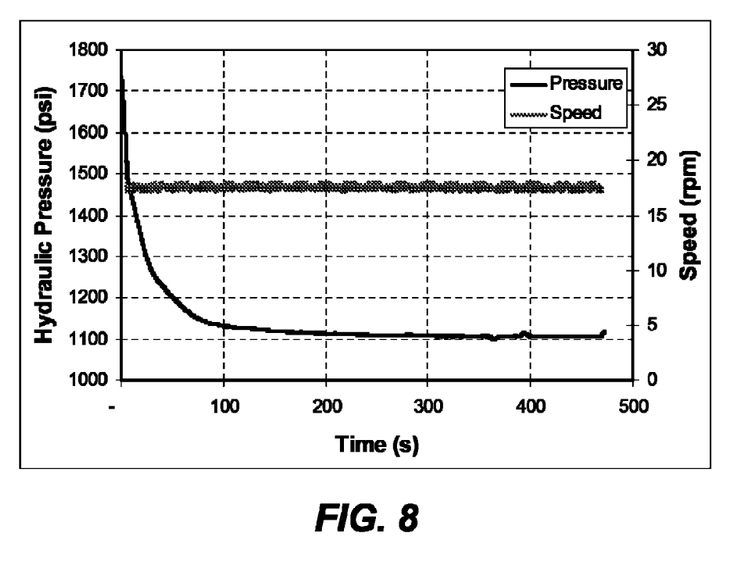
FIG. 8 is a graphic illustration showing the hydraulic pressure and drum rotation speed over time after the addition of cement dispersant.

After adding water or admixture to a load of cementitious material in the mixing drum, it is necessary to ensure that the concrete is fully mixed before calculating slump or slump flow. If the concrete is not fully mixed, part of the load may be highly fluid, whereas the rest of the load is significantly less fluid. Thus, the calculated slump or slump flow from drum mixer data would not be representative of the entire load. Full mixing can be ensured by specifying a certain number of drum turns or mixing time at certain speeds or by monitoring the hydraulic pressure and determining when the hydraulic pressure at a certain speed is constant over time. FIG. 8 indicates the decrease in average hydraulic pressure over time as the concrete is mixed at a constant drum rotation speed following the addition of cement dispersant. Slump or slump flow should only be calculated once a constant value of hydraulic pressure has been reached (after approximately 250 seconds in FIG. 8).

In further exemplary embodiments, the inventors believe it is possible to apply methods of the present invention to stationary mixing devices in concrete ready mix plants having a central stationary mixer, which could be operated using electrical power. Such a method would include (A) operating a central mixing apparatus located in a stationary plant and containing a hydratable cementitious material therein; (B) providing a sequence of values corresponding to the electrical power (e.g., amperage) required to operate the mixing apparatus or mixing blades/fins within the mixing apparatus at a particular speed $V^1$ and calculating an average value based on said sequence of values; (C) comparing said calculated average value to a set of average values at speed $V^1$ previously stored in computer memory storage location, said previously stored set containing values obtained from hydratable cementitious materials having predetermined slump flows at various slump flows within the range of 16 inches to 36 inches determined by measuring horizontal spread of cementitious material released from a slump cone; and (D) providing an indication of slump flow corresponding to said calculated average value provided in (B); adjusting the slump flow of said hydratable cementitious material in said mixing apparatus based on comparing said calculated average value to a set of average values previously stored in computer memory storage location; or performing a combination thereof.

While the invention is described herein using a limited number of embodiments, these specific embodiments are not intended to limit the scope of the invention as otherwise described and claimed herein. Modification and variations from the described embodiments exist. More specifically, the following examples are given as a specific illustration of embodiments of the claimed invention. It should be understood that the invention is not limited to the specific details set forth in the examples. All parts and percentages in the examples, as well as in the remainder of the specification, are by percentage weight unless otherwise specified.

Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, RL, and an upper limit RU, is disclosed, any number R falling within the range is specifically disclosed. In particular, the following numbers R within the range are specifically disclosed: R=RL+k*(RU−RL), where k is a variable ranging from 1% to 100% with a 1% increment, e.g., k is 1%, 2%, 3%, 4%, 5% ... 50%, 51%, 52% ... 95%, 96%, 97%, 98%, 99%, or 100%. Moreover, any numerical range represented by any two values of R, as calculated above, is also specifically disclosed.

Example 1

To ensure that a certain concrete mixture exhibits the correct workability and hardened properties, the concrete mixture with all ingredients except the cement dispersant must achieve a slump of 2 inches and the concrete mixture with all ingredients including the cement dispersant must achieve a slump flow of 27 inches. In this example (Table 1), all concrete ingredients except the cement dispersant were loaded into the rotating mixing drum and mixed initially. However, due to potential variations in water content, it was unknown during the batching process whether the volume of water added to the mixer was equal to the design water content. After initial mixing the slump was measured with automated slump monitoring equipment and determined to be 0.5 inches (step 1). Thus, sufficient water—in this example 25 gallons—was added to achieve a slump of 2.0 inches (step 2). Next, sufficient chemical was added to adjust the slump flow to the design value of 27 inches (step 3). In this case, the water content of the load was measured manually for confirmation. Specifically, the drum was emptied of all residual water, the water in aggregates was measured manually, and the additional water batched into the load was measured. During typical plant operations, the amount of water would not be measured directly because of the time-consuming nature of the process, but could be inferred based on achieving the correct slump. Optionally, the quantity of water and chemical could have been added in a single step after measuring the slump in step 1. Because the water and admixture contents were correct, the mixture did not exhibit segregation, as evaluated by measuring the visual stability index in accordance with ASTM C 1611. The visual stability index is assigned to a mix on a basis of 0 to 3, with mixtures assigned a 0 exhibiting no segregation and mixes assigned a 3 exhibiting extreme segregation. Mixtures with VSI greater than 1 are usually considered to be not segregation resistant.

TABLE 1

Example 1 data

| Step (after initial mixing) | Water Content (design = 272 gal) | Cement Dispersant Content | Slump (design = 2.0 in. without cement dispersant) | Slump Flow (design = 27 in. with cement dispersant) | Segregation |
|---|---|---|---|---|---|
| 1 | 243 gal | 0 gal | 0.5 in | N/A | No |
| 2 | 268 gal | 0 gal | 2.0 in. | N/A | No |
| 3 | 268 gal | 8.8 gal | N/A | 27 in. | No (VSI = 0.0) |

Example 2

In Example 2, the same concrete mixture design from Example 1 was batched. In this case, however, the initial slump was too high because too much water was added inadvertently (step 1). This high water content was measured manually in this example and was also reflected in the initial slump being greater than designed. In step 2, the cement dispersant was added to alter the mixture to a slump flow. Less cement dispersant was needed to reach the target slump flow than in Example 1 due to the higher water content. Even though the slump flow was very similar to that in Example 1, the VSI was 2.0, reflecting severe segregation of the concrete due to the high water content. Had the initial slump been achieved as the design slump, the mixture would not have segregated when the cement dispersant was added to reach a slump flow, as was the case in Example 1.

TABLE 2

Example 2 data

| Step (after initial mixing) | Water Content (design = 272 gal) | Cement Dispersant Content | Slump (design = 2.0 in. without cement dispersant) | Slump Flow (design = 27 in. with cement dispersant) | Segregation |
|---|---|---|---|---|---|
| 1 | 294 gal | 0 gal | 3.5 in | N/A | No |
| 2 | 294 gal | 7.1 gal | N/A | 29 in. | Yes (VSI = 2.0) |

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Skilled artisans can make variations and changes without departing from the spirit of the invention.

It is claimed:

1. A method for monitoring concrete, comprising:
   (A) rotating a mixing drum mounted on a delivery truck and having an inner drum surface upon which at least one mixing blade is attached such that said at least one mixing blade rotates with said mixing drum, said mixing drum containing concrete therein and being rotatable by a hydraulic system having charge and discharge ports, the delivery truck further having a first hydraulic pressure sensor on said charge port and a second hydraulic pressure sensor on said discharge port;
   (B) providing a sequence of values calculated as the difference between the charge and discharge pressure as sensed by said first and second hydraulic pressure sensors on said charge and discharge ports of the hydraulic system to rotate said mixing drum containing concrete at one particular speed $V^1$ and calculating an average value based on said sequence of values;

(C) comparing said calculated average value to a set of average values at speed $V^1$ previously stored in computer memory storage location, said previously stored set containing values obtained from concrete having predetermined slump flows at various slump flows within a range of 16 inches to 36 inches as determined by measuring horizontal spread of concrete released from a slump cone; and (D) providing an indication of slump flow corresponding to said calculated average value provided in (B); adjusting the slump flow of said concrete in said mixing drum based on comparing said calculated average value to a set of average values previously stored in computer memory storage location; or performing a combination thereof.

2. The method of claim 1 wherein, in providing an indication of slump flow corresponding to said calculated average value, said indication is provided by computer monitor display, printed paper output, or entry of data into computer memory storage location.

3. The method of claim 1 further comprising adjusting the slump flow of said concrete in said mixing drum based on comparing said calculated average value to a set of average values previously stored in computer memory storage location, by introducing a liquid into said concrete.

4. The method of claim 3 wherein said liquid introduced into said concrete comprises water, a chemical admixture, or a combination thereof.

5. The method of claim 4 further comprising monitoring the tilt or inclination of the mixing drum, concrete load size, temperature of the concrete, or combination thereof; and providing values corresponding to monitored tilt or inclination of the mixing drum, concrete load size, temperature of the concrete, or combination thereof.

6. The method of claim 5 further comprising adjusting the amount of said liquid introduced into said concrete based on said values corresponding to monitored tilt or inclination of the mixing drum, concrete load size, temperature of the concrete, or combination thereof.

7. The method of claim 4 wherein, in rotating the mixing drum containing concrete therein, the water content of said concrete is adjusted to achieve a predetermined slump within a range of 0 to 10 inches, and subsequently chemical cement dispersant is introduced to adjust said concrete to a pre-determined slump flow within a range of 16 to 36 inches.

8. The method of claim 7 wherein the predetermined slump is adjusted based on the concrete temperature.

9. The method of claim 4 wherein, in rotating the mixing drum containing concrete therein, water is introduced to adjust said concrete to a pre-determined slump flow within a range of 16 to 36 inches, and subsequent maintenance of slump flow over time is achieved by introducing a cement dispersant into the concrete rotated in the mixing drum and adjusting cement dispersant quantity introduced into the mixing drum.

10. The method of claim 4 wherein, the average value of hydraulic pressure required to rotate said concrete in the mixing drum at a particular speed $V^1$ is calculated after the average hydraulic pressure is constant over time, indicating the concrete and any added water or cement dispersant are fully mixed.

11. The method of claim 1 wherein, in comparing said calculated average value to a set of average values at speed $V^1$ previously stored in computer memory storage location, different calibration curves are used for different mixture designs.

12. A system for monitoring slump flow, comprising: a rotatable mixing drum mounted on a concrete delivery truck and having an inner surface upon which at least one mixing blade is attached such that at least one mixing blade rotates with said mixing drum for mixing concrete, said mixing drum being rotatable by a hydraulic system having charge and discharge ports, the delivery truck further having a first hydraulic pressure sensor on said charge port and a second hydraulic pressure sensor on said discharge port, a sensor for measuring rotational speed of said mixing drum, a computer processing unit configured for receiving values from both of said first and second hydraulic pressure sensors and for calculating the difference between the charge and discharge pressure as sensed by said first and second hydraulic pressure sensors, and for receiving values from said sensor for measuring rotational speed of said mixing drum, and computer memory storage location having stored therein a set of values obtained from concrete having predetermined slump flows at various slump flows within a range of 16 inches to 36 inches as determined by employing manual measurement of horizontal spread of concrete released from a removed slump cone.

* * * * *